US006824778B2

(12) United States Patent
Hart

(10) Patent No.: US 6,824,778 B2
(45) Date of Patent: Nov. 30, 2004

(54) PROPHYLACTIC AND THERAPEUTIC MONOCLONAL ANTIBODIES

(75) Inventor: Mary Kate Hart, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 32 days.

(21) Appl. No.: 10/127,641

(22) Filed: Apr. 22, 2002

(65) Prior Publication Data

US 2003/0099931 A1 May 29, 2003

Related U.S. Application Data

(60) Provisional application No. 60/285,601, filed on Apr. 23, 2001.

(51) Int. Cl.[7] ........................ A61K 39/42; C07K 16/08
(52) U.S. Cl. .............................. 424/147.1; 424/159.1; 530/388.3; 530/389.4
(58) Field of Search ........................... 530/388.3, 389.4; 424/147.1, 159.1, 218.1

(56) References Cited

PUBLICATIONS

Cruse et al. Illustrated Dictionary of Immunology, pp. 102–103. CRC Press, Boca Raton, FL, 1995.*

Ziemiecki et al (Journal of General Virology 50:111–123, 1980).*

Vaananen (Journal of Virological Methods 4:117–26, 1982).*

* cited by examiner

Primary Examiner—Mary E. Mosher
(74) Attorney, Agent, or Firm—Elizabeth Arwine

(57) ABSTRACT

In this application are described monoclonal antibodies which recognize E3 glycoprotein of alphavirus and epitopes recognized by these monoclonal antibodies. Also provided are mixtures of antibodies of the present invention, as well as methods of using individual antibodies or mixtures thereof for the detection, prevention, and/or therapeutical treatment of alphavirus infections in vitro and in vivo.

22 Claims, 4 Drawing Sheets

SEQUENCE LISTING

<160> NUMBER OF SEQ ID NOS: 5

<210> SEQ ID NO 1
<211> LENGTH: 55
<212> TYPE: PRT
<213> ORGANISM: Venezelan equine encephalitis virus IA

<400> SEQUENCE: 1

Ser Leu Val Thr Thr Met Cys Leu Leu Ala Asn Val Thr Phe Pro
 1               5                  10                  15

Cys Ala Gln Pro Pro Ile Cys Tyr Asp Arg Lys Pro Ala Glu Thr
                20                  25                  30

Leu Ala Met Leu Ser Val Asn Val Asp Asn Pro Gly Tyr Asp Glu
                35                  40                  45

Leu Leu Glu Ala Ala Val Lys Cys Pro Gly
                50                  55

<210> SEQ ID NO 2
<211> LENGTH: 55
<212> TYPE: PRT
<213> ORGANISM: Venezuelan Equine Encephalitis Virus IE

<400> SEQUENCE: 2

Ser Leu Val Thr Thr Met Cys Leu Leu Ala Asn Val Thr Phe Pro
 1               5                  10                  15

Cys Ser Gln Pro Pro Ile Cys Tyr Asp Arg Lys Pro Ala Glu Thr
                20                  25                  30

Leu Ser Met Leu Ser His Asn Ile Asp Asn Pro Gly Tyr Asp Glu
                35                  40                  45

Leu Leu Glu Ala Val Leu Lys Cys Pro Gly
                50                  55

<210> SEQ ID NO 3
<211> LENGTH: 55
<212> TYPE: PRT
<213> ORGANISM: Venezuelan equine encephalitis virus IIIA

<400> SEQUENCE: 3

Ser Leu Val Thr Thr Met Cys Leu Leu Ala Asn Val Thr Phe Pro
 1               5                  10                  15

Cys Ala Thr Pro Pro Ile Cys Tyr Asp Arg Ala Pro Ala Glu Thr
                20                  25                  30

Leu Met Met Leu Ser Lys Asn Ile Asp Asn Pro Gly Tyr Asp Glu
                35                  40                  45

Leu Leu Glu Ala Ala Val Lys Cys Pro Gly
                50                  55

<210> SEQ ID NO 4
<211> LENGTH: 56
<212> TYPE: PRT
<213> ORGANISM: Western equine encephalitis virus

<400> SEQUENCE: 4

Ser Leu Val Val Thr Ala Leu Cys Val Leu Ser Asn Val Thr Phe
 1               5                  10                  15

Pro Cys Asp Lys Pro Pro Val Cys Tyr Ser Leu Ala Pro Glu Arg
                20                  25                  30

Thr Leu Asp Val Leu Glu Glu Asn Val Asp Asn Pro Asn Tyr Asp

```
                       35                  40                  45
Thr Leu Leu Glu Asn Val Leu Lys Cys Pro Ser
                50                  55

<210> SEQ ID NO 5
<211> LENGTH: 58
<212> TYPE: PRT
<213> ORGANISM: Eastern equine encephalitis virus

<400> SEQUENCE: 5

Ser Leu Ala Thr Val Met Cys Val Leu Ala Asn Ile Thr Phe Pro
 1               5                  10                  15

Cys Asp Gln Pro Pro Cys Met Pro Cys Cys Tyr Glu Lys Asn Pro
                20                  25                  30

His Glu Thr Leu Thr Met Leu Glu Gln Asn Tyr Asp Ser Arg Ala
                35                  40                  45

Tyr Asp Gln Leu Leu Asp Ala Ala Val Lys Cys Asn Ala
                50                  55
```

US 6,824,778 B2

PROPHYLACTIC AND THERAPEUTIC MONOCLONAL ANTIBODIES

This application claims benefit of priority from an earlier filed Provisional application Ser. No. 60/285,601 filed on Apr. 23, 2001, now abandoned.

INTRODUCTION

Infection with Venezuelan equine encephalitis (VEE) virus causes an incapacitating febrile illness in people. Two vaccines (TC-83 and C-84) are currently available for human use as Investigational New Drugs, but both have limitations that prompted the development of an improved vaccine candidate. Unlike TC-83 and C-84, this new vaccine candidate (V3526) has a deletion of the PE2 glycoprotein cleavage site and a suppressor mutation at E1-253 (Davis et al., 1995, Virology 212: 102–110.).

Alphaviruses have protein spikes on their envelope which function during attachment of the virus to a cell. Three E1:E2 heterodimers associate to form one VEE virus glycoprotein spike. Normally, the E2 glycoprotein is cleaved at a furin-sensitive RKRR sequence from a PE2 precursor composed of E2 and E3 combined. Cleavage is believed to occur in the golgi or at the cell membrane, resulting in the production of E2 and E3 glycoproteins. The E3 glycoprotein is not present in the mature VEE virion. However, the deletion of the PE2 cleavage site in the V3526 candidate results in mature virions with spikes containing heterodimers of PE2 (without the RKRR cleavage sequence) and E1. The presence of the E3 protein in the spike could theoretically have profound implications on the ability of this virus to serve as a vaccine, by obscuring or altering the conformation of protective epitopes on the virus. However, animal studies (Davis et al., 1995, supra; Hart et. al., 2000, Vaccine 18, 3067–3075) indicate that V3526 induces protective immunity, such that V3526 remains a potential vaccine candidate. Alternatively, the inclusion of E3 in the spike could provide the immune system greater access to epitopes on this protein that would normally only be present as soluble protein either after PE2 cleavage or when infected cells lyse.

In order to identify potentially important epitopes on the E3 glycoprotein, monoclonal antibodies to V3526 were generated in 1994. Hybridoma supernatants were screened by ELISA for preferential binding to V3526 compared to VEE virus that cleaves the E3 protein (VEE Trinidad, TrD). Most of the 138 supernatants reacted equally to V3526 and TrD in ELISA and were not further evaluated. Six hybridomas were cloned twice and characterized. Surprisingly, the Mabs produced from these hybridomas, 13D4, 5E2, 5E4, 10D6, 10D7 and 3F2, notably 13D4, were found to protect mice from a lethal challenge with Venezuelan equine encephalitis (VEE) virus. The finding that Mabs with this specificity are protective is novel in that the E3 protein is normally cleaved from its precursor in infected cells and is not associated with most mature alphaviruses, and would not be expected to be a target of protective antibodies.

SUMMARY OF THE INVENTION

Therefore, this application describes protective VEE E3-specific MAbs. The antibodies are classified into one competition group based on competitive binding assays. One monoclonal antibody, namely, 13D4 protected BALB/c mice from death after challenge with virulent VEE virus when at least 20 ug of MAb was administered to the mice prior to challenge. The other five MAbs generally protected fewer than half of the recipient mice, even when a 50 ug dose of MAb was administered, although the mean time to death was extended significantly in these mice relative to control mice. The MAbs of the present invention may be used as a prophylactic or therapeutic treatment for alphavirus infections in other animal species, or in people. In addition, these Mabs may be used to distinguish in vitro between alphaviruses that have cleaved E3 and those that have not. This could be especially useful for diagnostic assays or in assays where the virus with E3 needs to be specifically neutralized.

Therefore, it is an object of the present invention to provide monoclonal antibodies which protect against VEE virus and bind to epitopes on the VEE virus E3 protein. Such antibodies are, for instance, produced by the cell line VE-V 13D4-1-1 deposited under the Budapest Treaty at American Type Culture Collection, Manassas, Va. on Apr. 14, 2002, having ATCC accession no. PTA-4248, and hybridoma cell line VE-V 5E2-1-1 deposited on Feb. 12, 2004, having ATCC accession no. PTA-5813, and hybridoma cell line VE-V 10D6-1-1 deposited on Feb. 12, 2004, having ATCC accession no. PTA-5814.

It is another object of the invention to provide for antibodies that are functionally equivalent to the antibodies listed above. These functionally equivalent antibodies substantially share at least one major functional property with an antibody listed above and herein described comprising: binding specificity to E3, protection against VEE challenge when administered prophylactically or therapeutically, or competition for the same binding site on E3. The antibodies can be of any class such as IgG, IgM, or IgA or any subclass such as IgG1, IgG2a, and other subclasses known in the art. Further, the antibodies can be produced by any method, such as phage display, or produced in any organism or cell line, including bacteria, plant, insect, mammal or other type of cell or cell line which produces antibodies with desired characteristics, such as humanized antibodies. The antibodies can also be formed by combining an Fab portion and a Fc region from different species.

The monoclonal antibodies of the present invention described below recognize epitopes on E3. The immunogen was the vaccine virus V3526 (Davis et al., 1995, Virology 212, 102–110; Hart et al., 2000. Vaccine 18, 3067–3075; Hart et al., 2002, Vaccine 20, 616–22; Steele et al., 1998, Vet. Pathl. 35, 386–97).

The sequence of the E3 protein which is not processed into E2, i.e. which do not contain a cleavage site, is presented below for different alphaviruses. These sequences/peptides can be used as immunogens for the production of protective antibodies, polyclonal or monoclonal, which recognize E3 of the different alphaviruses listed. The method for generating antibodies using peptides is well known in the art.

```
VEE IA                                    (SEQ ID NO:1)
SLVT-TMCLLANVTFPCAQP - - -
PICYDRKPAETLAMLSVNVDNPGYDELLEAAVKCPG

VEE IE                                    (SEQ ID NO:2)
SLVT-TMCLLANVTFPCSQP - - -
PICYDRKPAETLSMLSHNIDNPGYDELLEAVLKCPG

VEE IIIA                                  (SEQ ID NO:3)
SLVT-TMCLLANVTFPCATP - - -
PICYDRAPAETLMMLSKNIDNPGYDELLEAAVKCPG
```

```
                       -continued
WEE                                                  (SEQ ID NO:4)
SLVVTALCVLSNVTFPCDKP - - -
PVCYSLAPERTLDVLEENVDNPNYDTLLENVLKCPS EEE                                                  (SEQ ID NO:5)
SLAT-
VMCVLANITFPCDQPPCMPCCYEKNPHETLTMLEQNYDSRAYDQLLDAAV
KCNA
```

It is another object of the present invention to provide for mixtures of antibodies according to the present invention, as well as to methods of using individual antibodies, or mixtures thereof for the prevention and/or therapeutic treatment of VEE infections in vitro and in vivo, and/or for improved detection of VEE infections.

It is yet another object of the present invention to treat or prevent VEE virus infection by administering a therapeutically or prophylactically effective amount of one antibody of the present invention or a mixture of antibodies of the present invention to a subject in need of such treatment.

It is another object of the present invention to provide passive vaccines for treating or preventing VEE virus infections comprising a therapeutically or prophylactically effective amount of the antibodies of the present invention which protect against VEE virus, in combination with a pharmaceutically acceptable carrier or excipient. In a related aspect, similar antibodies generated from other alphaviruses can be similarly used as passive vaccines for treating or preventing such alphavirus infections.

It is still another object of the present invention to provide novel immunoprobes and test kits for detection of VEE virus which does not cleave its PE2 precursor, i.e. retains the E3 protein. For immunoprobes, the antibodies are directly or indirectly attached to a suitable reporter molecule, e.g., and enzyme or a radionuclide. The test kit includes a container holding one or more antibodies according to the present invention and instructions for using the antibodies for the purpose of binding to said VEE virus to form an immunological complex and detecting the formation of the immunological complex such that presence or absence of the immunological complex correlates with presence or absence of said VEE virus.

It is another object of the present invention to provide anti-idiotypic antibodies raised against one of the present monoclonal antibodies for use as a vaccine to elicit an active anti-E3 response.

It is yet another object of the present invention to provide antigenic epitopes as a component of a alphavirus vaccine. The epitopes described above comprising SEQ ID NO:1–5, or conservative changes thereof which are still recognized by the antibodies, are useful for actively immunizing a host to elicit production of protective antibodies against alphaviruses.

BRIEF DESCRIPTION OF THE DRAWINGS

These and other features, aspects, and advantages of the present invention will become better understood with reference to the following description and appended claims, and accompanying drawings where:

DETAILED DESCRIPTION

Figure 1A:
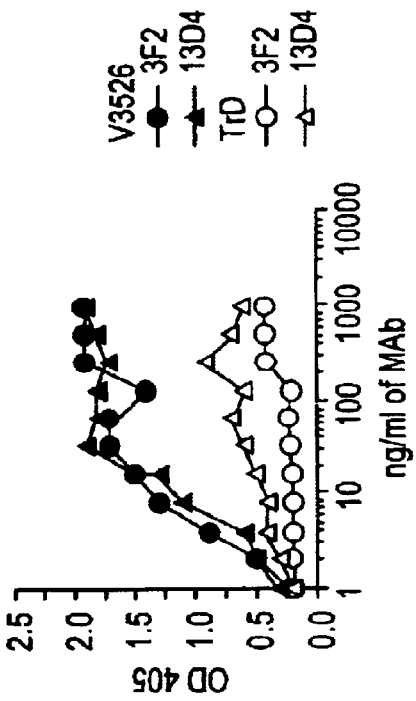
FIGS. 1A, 1B, 1C and 1D. Relative binding of anti-V3526 MAbs to VEE viruses in ELISA. ELISA data obtained against V3526 (solid) or TrD (open) viruses are shown for anti-V3526 MAbs: 10D6 and 10D7 (A), 3F2 and 13D4 (B) and 5E2 and 5E4 (C). Anti-E2c was used as a positive control, while irrelevant isotype-matched MABs were used as negative controls (D). The mean O.D. 405 valued obtained for duplicate wells at each tested concentration after subtracting the mean plate value (0.1) O.D. are shown. The difference between duplicate wells did not exceed 0.3 O.D. units.
Figure 1B:
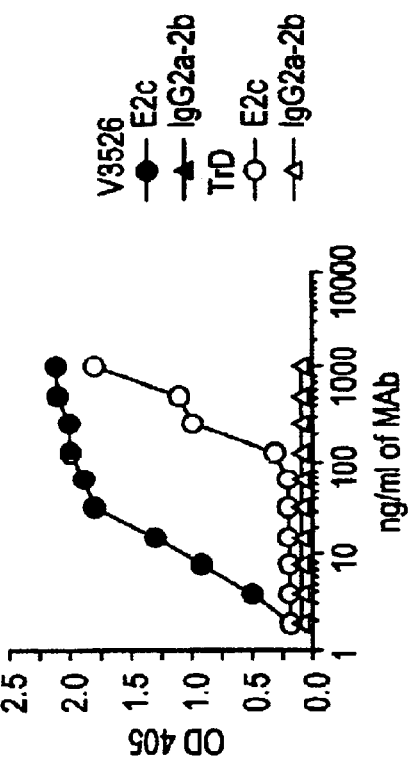
Figure 1C:
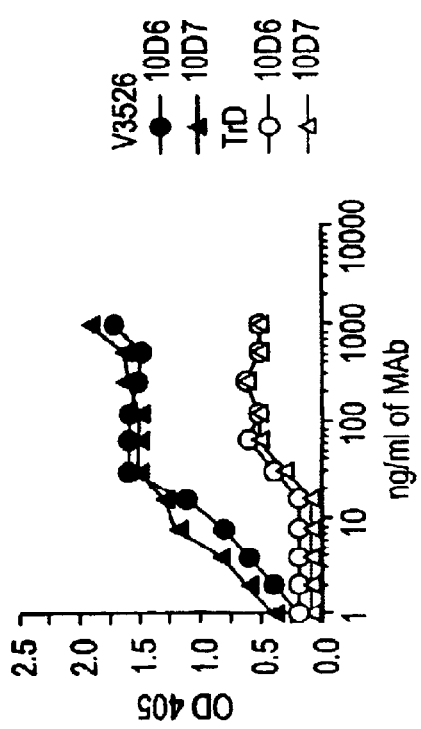
Figure 1D:
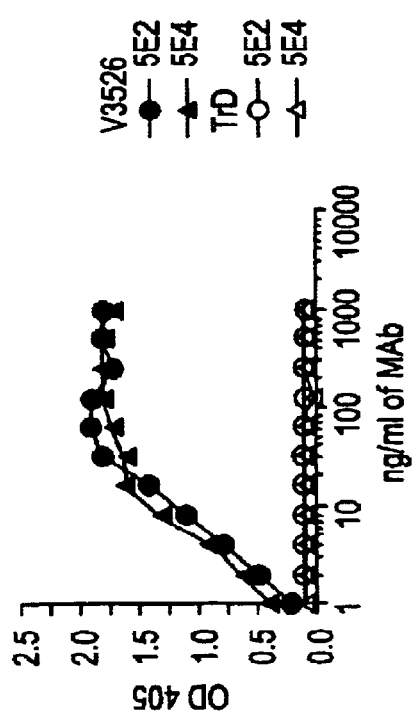

In the description that follows, a number of terms used in recombinant DNA, virology and immunology are extensively utilized. In order to provide a clearer and consistent understanding of the specification and claims, including the scope to be given such terms, the following definitions are provided.

Alphaviruses. The genome of alphaviruses is a single-stranded, plus-sense RNA approximately 11,400 nucleotides in length. The 5' two-thirds of the genome consist of a non-coding region of approximately 48 nucleotides followed by a single open reading frame of approximately 7,500 nucleotides which encode the viral replicase/transcriptase. The 3' one-third of the genome encodes the viral structural proteins in the order C-E3-E2–6K-E1, each of which are derived by proteolytic cleavage of the product of a single open reading frame of approximately 3700 nucleotides. The sequences encoding the structural proteins are transcribed as a 26S mRNA from an internal promoter on the negative sense complement of the viral genome. The nucleocapsid (C) protein possesses autoproteolytic activity which cleaves the C protein from the precursor protein soon after the ribosome transits the junction between the C and E3 protein coding sequence. Subsequently, the envelope glycoproteins E2 and E1 are derived by proteolytic cleavage in association with intracellular membranes and form heterodimers. E2 initially appears in the infected cell as a precursor, pE2, which consists of E3 and E2. After extensive glycosylation and transit through the endoplasmic reticulum and the golgi apparatus, E3 is cleaved from E2 by furin-like protease activity at a cleavage site consisting of RKRR with the cleavage occuring after the last arginine residue. Subsequently, the E2/E1 complex is transported to the cell surface where it is incorporated into virus budding from the plasma membrane (Strauss and Strauss, 1994).

The term "antibody" is art-recognized terminology and is intended to include molecules or active fragments of molecules that bind to known antigens. Examples of active fragments of molecules that bind to known antigens include Fab and F(ab')$_2$ fragments. These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. *J. Nucl. Med.* 23:1011–1019 (1982). The term "antibody" also includes bispecific and chimeric antibodies.

The language "monoclonal antibody" is art-recognized terminology. The monoclonal antibodies of the present invention can be prepared using classical cloning and cell fusion techniques. The immunogen (antigen) of interest is typically administered (e.g. intraperitoneal injection) to wild type or inbred mice (e.g. BALB/c) or transgenic mice which produce desired antibodies, rats, rabbits or other animal species which can produce native or human antibodies. The immunogen can be administered alone, or mixed with adjuvant, or expressed from a vector (VEE replicon vector, vaccinia), or as DNA, or as a fusion protein to induce an immune response. Fusion proteins comprise the peptide against which an immune response is desired coupled to carrier proteins, such as β-galactosidase, glutathione S-transferase, keyhole limpet hemocyanin (KLH), and bovine serum albumin, to name a few. In these cases, the peptides serve as haptens with the carrier proteins. After the animal is boosted, for example, two or more times, the spleen is removed and splenocytes are extracted and fused with myeloma cells using the well-known processes of Kohler and Milstein (*Nature* 256: 495–497 (1975)) and Harlow and Lane (*Antibodies: A Laboratory Manual* (Cold Spring Harbor Laboratory, New York 1988)). The resulting hybrid cells are then cloned in the conventional manner, e.g. using limiting dilution, and the resulting clones, which produce the desired monoclonal antibodies, cultured.

The term "epitope" is art-recognized. It is generally understood by those of skill in the art to refer to the region of an antigen or antigens, that interacts with an antibody. An epitope of a peptide or protein antigen can be formed by contiguous or noncontinguous amino acid sequences of the antigen. E3, or pE2, like many proteins, contains many epitopes. The epitopes or peptides recognized by the antibodies of the present invention and conservative substitutions of these peptides which are still recognized by the antibody are an embodiment of the present invention. These peptides offer a convenient method for eluting E3 or pE2 to MAb 13D4, 5E2, 5E4, 10D6, 10D7, and 3F2 on immunoaffinity columns. For example, when an antibody which recognizes the epitope for MAb 13D4 is used in an immunoaffinity column to purify pE2, the peptide recognized by the antibody can be added to the immunoaffinity column to elute the pE2. Further truncation of these epitopes may be possible since antigenic epitopes have been reported to be represented by as few as five amino acid residues.

Epitope mapping studies described in this application show that 13D4 recognizes conformational epitopes comprising discontinuous VEE virus amino acids. Antibodies which compete with MAb 13D4 are considered to recognize discontinuous epitopes and are considered equivalent to the antibodies of the present invention. Assays for determining whether or not an antibody competes with an antibody of the present invention are known to a person with ordinary skill in the art and are described below.

By further mapping of the binding site of the monoclonal antibodies described in this application other peptides useful as a vaccine or a therapeutic can be predicted. Therefore, in another aspect, this invention relates to a method for identifying protective antigenic epitopes, the method comprising (i) reacting a monoclonal antibody described in this application to different overlapping fragments encompassing the complete antigen, (ii) identifying a fragment to which the protective antibody binds, (iii) narrowing the region containing sites further by reacting the monoclonal with smaller overlapping fragments encompassing the region identified in (ii), and (iv) choosing peptides to which the antibody binds as possible antigenic epitopes. The peptides can then be assayed for their ability to protect an animal from disease, or to reduce the severity of disease. Peptides defining antigenic protective epitopes can be used in a vaccine as described below and in the Examples.

The epitopes or peptides to which the monoclonal antibodies of the present invention bind can constitute all or part of an eventual active vaccine candidate. An active vaccine or therapeutic candidate might comprise these peptide sequences and others. These might be delivered as synthetic peptides, or as fusion proteins, alone or co-administered with cytokines and/or adjuvants or carriers safe for human use, e.g. aluminum hydroxide, to increase immunogenicity. In addition, sequences such as ubiquitin can be added to increase antigen processing for more effective immune responses.

The present invention also pertains to hybridomas producing antibodies which bind to an epitope of alphavirus pE2. The term "hybridoma" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above and the Examples below for a more detailed description of the method of fusion.

The present invention still further pertains to a method for detecting alphavirus E3 in a sample suspected of containing alphavirus E3. The method includes contacting the sample with an antibody which binds an epitope of E3, allowing the antibody to bind to E3 to form an immunological complex, detecting the formation of the immunological complex and correlating the presence or absence of the immunological complex with the presence or absence of E3 in the sample. The sample can be biological, environmental or a food sample.

The language "detecting the formation of the immunological complex" is intended to include discovery of the presence or absence of E3 in a sample. The presence or absence of E3 can be detected using an immunoassay. A number of immunoassays used to detect and/or quantitate antigens are well known to those of ordinary skill in the art. See Harlow and Lane, *Antibodies: A Laboratory Manual* (Cold Spring Harbor Laboratory, New York 1988 555–612). Such immunoassays include antibody capture assays, antigen capture assays, and two-antibody sandwich assays. These assays are commonly used by those of ordinary skill in the art. In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from an alphavirus vaccinee and a monoclonal antibody of the present invention, are allowed to compete for binding of the antigen. The amount of monoclonal bound is then measured, and a determination is made as to whether the serum contains anti E3 antibodies. This competitive ELISA can be used to indicate immunity to known protective epitopes in a vaccinee following vaccination and to identify competing antibodies.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen.

These immunoassays typically rely on labeled antigens, antibodies, or secondary reagents for detection. These proteins can be labeled with radioactive compounds, enzymes, biotin, or fluorochromes. Of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (*Clin. Chim. Acta* 70:1–31), and Schurs, A. H. W. M., et al. 1977 (*Clin. Chim Acta* 81:1–40). Coupling techniques mentioned in the latter are the glutaraldehyde method, the periodate method, the dimaleimide method, and others, all of which are incorporated by reference herein.

The language "biological sample" is intended to include biological material, e.g. cells, tissues, biological fluid, or a solution for administering to a subject, such as a vaccine, or immunoglobulin. By "environmental sample" is meant a sample such as soil and water. Food samples include canned goods, meats, and others.

Yet another aspect of the present invention is a kit for detecting E3 in a biological sample. The kit includes a container holding one or more antibodies which binds an epitope of E3 and instructions for using the antibody for the purpose of binding to E3 to form an immunological complex and detecting the formation of the immunological complex such that the presence or absence of the immunological complex correlates with presence or absence of E3 in the sample. Examples of containers include multiwell plates which allow simultaneous detection of E3 in multiple samples.

As described in greater detail in the examples, the present inventors have isolated six monoclonal antibodies which bind to epitopes on E3 and display in vitro and/or in vivo virus protective properties. Significantly, the reactivity of the MAbs is applicable against a broad variety of different wild type and laboratory alphavirus strains of different types as determined in vitro using ELISA, western blot, radioimmunoprecipitation, plaque reduction tests; or in vivo against challenge with virulent virus. Wild type strains include for example IA/B Trinidad donkey, IE 68U201, IIIA (Mucambo), WEE CBA IIIA, and EEE FLA. Laboratory strains can be derived from wild type strains and include those which have been passaged such as TC-83 or animal adapted strains, and those derived by site-directed mutagenesis to retain E3: V3526, VE1150k (VEE IE), VEE IIIA (4203, 4204, 4208), W2102 (negative based on in vitro data), and other WEE strains 2130 and 2103.

Given these results, monoclonal antibodies according to the present invention are suitable both as therapeutic and prophylactic agents for treating or preventing alphavirus infection in susceptible alphavirus-infected subjects. Subjects include rodents such as mice or guinea pigs, monkeys, and other mammals, including humans.

In general, this will comprise administering a therapeutically or prophylactically effective amount of one or more monoclonal antibodies of the present invention to a susceptible subject or one exhibiting alphavirus infection. Any active form of the antibody can be administered, including Fab and F(ab')$_2$ fragments. Antibodies of the present invention can be produced in any system, including insect cells, baculovirus expression systems, chickens, rabbits, goats, cows, or plants such as tomato, corn, potato, banana or strawberry. Methods for the production of antibodies in these systems are known to a person with ordinary skill in the art. Preferably, the antibodies used are compatible with the recipient species such that the immune response to the MAbs does not result in clearance of the MAbs before virus can be controlled, and the induced immune response to the MAbs in the subject does not induce "serum sickness" in the subject. Preferably, the MAbs administered exhibit some secondary functions such as binding to Fc receptors of the subject.

Treatment of individuals having alphavirus infection may comprise the administration of a therapeutically effective amount of 13D4 antibodies of the present invention. The antibodies can be provided in a kit as described below. The antibodies can be used or administered as a mixture, for example in equal amounts, or individually, provided in sequence, or administered all at once. In providing a patient with antibodies, or fragments thereof, capable of binding to E3, or an antibody capable of protecting against alphavirus in a recipient patient, the dosage of administered agent will vary depending upon such factors as the patient's age, weight, height, sex, general medical condition, previous medical history, etc.

In general, it is desirable to provide the recipient with a dosage of antibody which is in the range of from about 1 pg/kg–100 pg/kg, 100 pg/kg–500 pg/kg, 500 pg/kg–1 ng/kg, 1 ng/kg–100 ng/kg, 100 ng/kg–500 ng/kg, 500 ng/kg–1 ug/kg, 1 ug/kg–100 ug/kg, 100 ug/kg–500 ug/kg, 500 ug/kg–1 mg/kg, 1 mg/kg–50 mg/kg, 50 mg/kg–100 mg/kg, 100 mg/kg–500 mg/kg, 500 mg/kg–1 g/kg, 1 g/kg–5 g/kg, 5 g/kg–10 g/kg (body weight of recipient), although a lower or higher dosage may be administered.

In a similar approach, another therapeutic use of the monoclonal antibodies of the present invention is the active immunization of a patient using an anti-idiotypic antibody raised against one of the present monoclonal antibodies. Immunization with an anti-idiotype which mimics the structure of the epitope could elicit an active anti-E3 response (Linthicum, D. S. and Farid, N. R., Anti-Idiotypes, Receptors, and Molecular Mimicry (1988), pp 1–5 and 285–300).

Likewise, active immunization can be induced by administering one or more antigenic and/or immunogenic epitopes as a component of a subunit vaccine. Vaccination could be performed orally or parenterally in amounts sufficient to enable the recipient to generate protective antibodies against this biologically functional region, prophylactically or therapeutically. The host can be actively immunized with the antigenic/immunogenic peptide, with or without adjuvant, in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cyteine and derivatives thereof. Alternative protein modification techniques may be used e.g., $NH_2$-acetylation or COOH— terminal amidation, to provide additional means for coupling or fusing the peptide to another protein or peptide molecule or to a support.

The antibodies capable of protecting against alphavirus are intended to be provided to recipient subjects in an amount sufficient to effect a reduction in the alphavirus infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a phamaceutically acceptable carrier vehicle. Suitable vehicles and their formulation, inclusive of other human proteins, e.g., human serum albumin, are described, for example, in Remington's Pharmaceutical Sciences (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Controlled release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacylate)-microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Administration of the antibodies disclosed herein may be carried out by any suitable means, including parenteral injection (such as intraperitoneal, subcutaneous, or intramuscular injection), in ovo injection of birds, orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation.

The treatment may be given in a single dose schedule, or preferably a multiple dose schedule in which a primary course of treatment may be with 1–10 separate doses, followed by other doses given at subsequent time intervals required to maintain and or reinforce the response, for example, at 1–4 months for a second dose, and if needed, a subsequent dose(s) after several months. Examples of suitable treatment schedules include: (i) 0, 1 day, and 6 days (ii) 0, 7 days and 1 month, (iii) 0 and 1 month, (iv) 0 and 6 months, (v) 0, 1 month and 6 months, or other schedules sufficient to elicit the desired responses expected to reduce disease symptoms, or reduce severity of disease.

The present invention also provides kits which are useful for carrying out the present invention. The present kits comprise a first container means containing the above-described antibodies. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following MATERIALS AND METHODS were used in the examples that follow.

Hybridoma production. Specific pathogen-free female BALB/c mice (National Cancer Institute, Frederick, Md.) were vaccinated intraperitoneally with $2 \times 10^5$ plaque forming units of V3526 virus in 0.2 ml sterile phosphate-buffered saline. Four weeks later, mice were inoculated intravenously with 40 ug of irradiated ($6 \times 10^6$ RAD), sucrose gradient-purified V3526 virus in 0.2 ml phosphate-buffered saline. Three days later, mice were euthanized and the spleens removed and teased into single cell suspensions which were fused to P3X63 Ag8.653 myeloma cells using previously described techniques (Stiles et al., 1991, Toxicon 29: 1195–1204). Supernatants from wells containing cells were screened by enzyme linked immunosorbent assay (ELISA) for reactivity with V3526 and virulent, PE2-cleaving Trinidad donkey (TrD) viruses. Hybridomas with better reactivity with V3526 than TrD were cloned twice.

ELISA. 96-well polyvinyl microtiter plates (Falcon 3912) were coated overnight at 40C with 0.5 mg of sucrose gradient-purified virus per well in 35 mM NaHCO3, 15 mM Na2CO3 (pH 9.6). Plates were washed and blocked with bovine serum albumin blocking buffer (Kirkegaard-Perry Laboratories, Inc., Gaithersburg, Md.) before adding samples, which were allowed to bind to antigen-coated wells overnight at 40° C. Heavy chain-specific, alkaline phosphatase-labelled anti-mouse secondary antibody was added to washed plates and permitted to react at room temperature for 1 hr. Substrate (1 mg/ml p-nitrophenyl phosphate (Sigma Chemical Co., St. Louis, Mo.) dissolved in 1 M Tris-0.02M MgCl2) was added to washed plates for 45 min at room temperature. The absorbance at 405 nm was determined with a Dynatech MR5000 microplate reader (Sunnyvale, Calif.). Endpoint titers were determined as the last threefold dilution with an absorbance three times higher than that of medium-inoculated controls.

For competitive binding assays, reactivity of unlabelled antibody (serially diluted 3-fold from 2 ug to 0.001 ug/well) with the virus-coated plates was evaluated in the absence or presence of 2 ng/well biotin-labelled competing antibody, developed with 100 ul/well of peroxidase-labelled Strep-Avidin (Amersham, diluted 1:2000), and the absorbance determined at 410 and 490 nm.

Plaque-Reduction Neutralization Test (PRNT). Virus-neutralizing antibody responses were titrated using V3526 or virulent V3000 VEE virus. Sera were serially diluted twofold and incubated overnight with virus. The serum-virus mixtures were further incubated on Vero cell monolayers for 1 hr. Wells were overlaid with 0.6% agarose in complete EBME (Eagle's basal medium with Earle's salts supplemented with 10% fetal bovine serum, 200 IU/ml penicillin, 200 mg/ml streptomycin, 100 mM L-glutamine, and 100 mM nonessential amino acids). Plaques were developed with neutral red stain 1 day later. The endpoint titer was determined to be the highest dilution with an 80% or greater reduction (PRNT 80) of the number of plaques observed in control wells.

Immunoprecipitation and western blotting. Confluent baby hamster kidney (BHK) cells were infected at a multiplicity of infection of 20 with virus and incubated for 5 hr at 37° C. and 5% $CO_2$ for labelled lysates, or 8 hrs for unlabelled lysates. Unlabelled lysates were made by freezing and thawing cells three times. For labelled lysates, cells were washed in cysteine and methionine-free Dulbecco's minimal essential medium (DMEM) and supplemented with 10 ml of DMEM containing 50 uCi each of $^{35}$S-Cysteine (48 T Bq/mol) and $^{35}$S-Methionine (37 T Bq/mol) (Amersham) for 4 hr at 37° C. and 5% $CO_2$ and then with 100X unlabelled cysteine and methionine for 30 min at 37° C. The cells were rinsed in NET (150 mM NaCl, 5 mM EDTA, 50 mM Tris, pH 8.0) and lysed at 37° C. for 5 min with 2.5 ml NET supplemented with 2% Triton X-100, 1% deoxycholic acid, 9 ug/ml phenylmethylsulfonyl fluoride, 5 ug/ml each of pepstatin and leupeptin, and 50 ug each of chymostatin, antipain, and aprotinin. The lysate was centrifuged at 25,000×g for 30 min at 4° C.

For immunoprecipitations, Mabs were added to protein A-Sepharose beads and then added to 0.25 ml labelled cell lysate overnight at 4° C. After washing, 50 ul sample buffer (Laemmli 1970) was added, the samples were boiled for 5 min and 25 ul added to each lane of a 12.5% or 15% SDS-polyacrylamide gel as described in Laemmli 1970 but using a 30:0.08 ratio of acrylamide/N,N'Diallytartardiamide. For western blotting, 1 ml of virus-infected cell lysates was added to each gel. Viral proteins were separated by electrophoresis at 250 volts for 3.5 hrs.

Immunoprecipitation gels were soaked in 500 ml of 20% trichloroacetic acid for 20 min and then in dimethylsulfoxide (DMSO) for 3 min, 60 min and 30 min, and then in DMSO with 20% organic scintillator (2,5-diphenyloxazole) for 90 min. The DMSO was replaced with distilled water for 20 min. The gel was dried for 2 hr at 80° C. on a Hoeffer slab gel dryer and then Ektascan MC film was exposed to the gel for up to 5 weeks at −70° C.

For western blots, proteins were transferred from the gel to 0.45 um nitrocellulose using a semi-dry Pharmacia/LKB Multiphor II system at 177 mA for 2 hr. Nitrocellulose was then blocked overnight at 4° C. with PBS supplemented with 5% nonfat dry milk and 0.05% Tween 20, and then washed. Mabs at 1 ug/ml or anti-VEE hyperimmune ascitic fluid diluted 1:1000 were added to nitrocellulose strips and incubated overnight at 4° C. while rocking. They were washed, incubated with horseradish peroxidase-labelled goat anti-mouse IgG for 1 hr at 37° C., washed and developed with ECL (Amersham #RPN2108) substrate and exposed to film at room temperature for 10 min or less.

Genosys spots membranes. Overlapping peptides spanning the VEE E3 sequence were synthesized on membranes by Genosys. Reactivity of Mabs with the peptides was tested by rinsing the membrane in 100% methanol for 1 minute then in PBS-0.05% Tween 20 for 10 min at room temperature. The membrane was blocked overnight at 4° C. in PBS-5% non-fat dry milk-0.05% Tween 20, washed and incubated with Mab (5 ug/ml) for 1 hr at room temperature. The membrane was washed three times and incubated with peroxidase-labelled goat anti-mouse IgG, IgA, IgM for 1 hr at room temperature. The membrane was washed and ECL added as for western blots and developed for one minute.

Passive transfer and challenge studies. BALB/c mice were injected intraperitoneally with Mab (0.2 ml) and bled 20 hours later, followed by challenge 5 hrs later with $1 \times 10^4$ plaque forming units of TrD virus administered intraperitoneally.

EXAMPLE 1

Figure 2A:
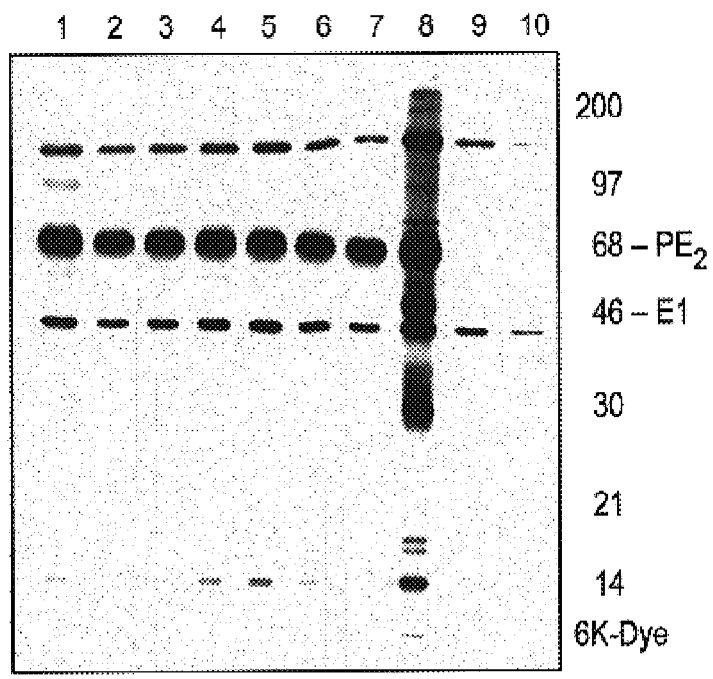
FIGS. 2A and 2B. SDS-PAGE gel analysis of REPs using anti-V3526 MAbs. Electrophoresis was performed using 15% gels to identify viral proteins precipitated by anti-V3526 MAbs from $^{35}$S-labeled lysates of A) V3526- and B) TrD-infected cells after a 36 hour exposure. Anti V3526 MAbs 3F2, 5E2, 10D6, 10D7, 13D4 and 5E4 are shown in lanes 1–6 respectively. Anti-E2$^c$ (lane 7) and MAbs HMAF (lane 8) are positive controls, while irrelevant isotype-matched MAbs (lanes 9 and 10) are negative controls. $^{14}$C rainbow high and low molecular weight markers are labeled on the right.
Figure 2B:
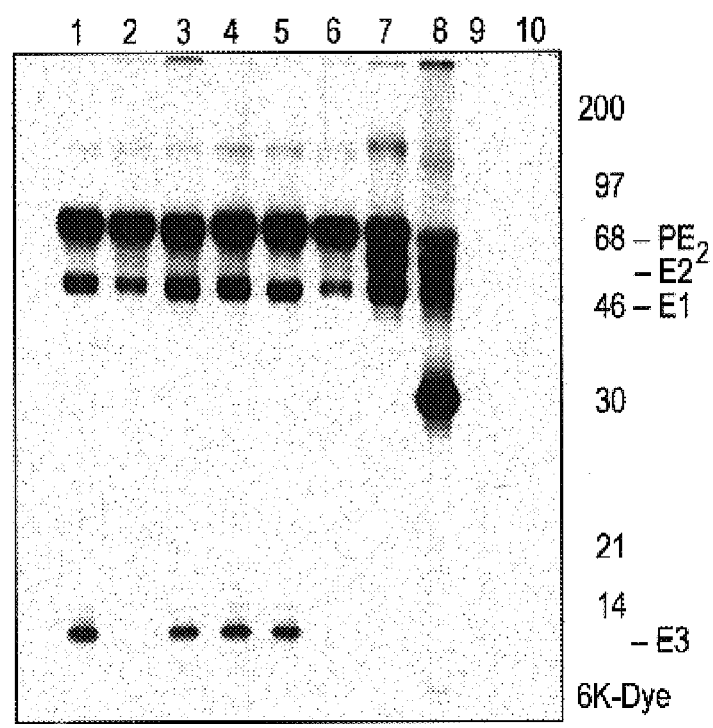
Figure 3A:
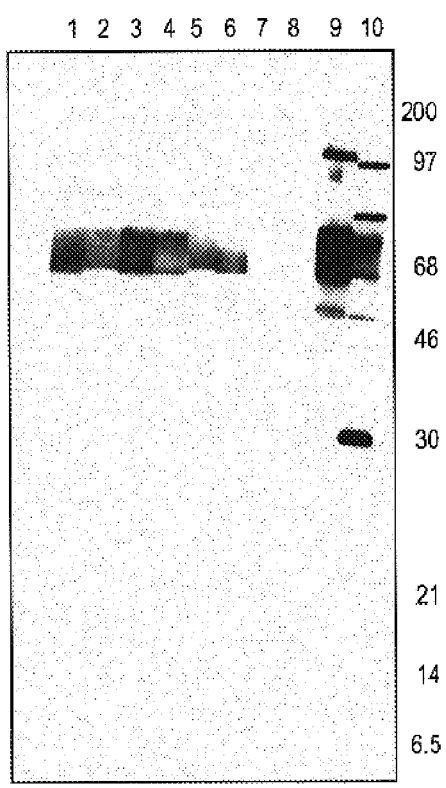
FIGS. 3A and 3B. Viral protein specificity of anti-V3526 MAbs in western blots. Electrophoresis was performed using 15% gels to identify viral proteins bound by anti-V3526 MAbs in western blots using A)V3526- and B) TC-83-infected cell lysates. Anti-V3526 MAbs 3F2, 5E2, 10D6, 10D7, 13D4 and 5E4 (1 ug/ml) are shown in laned 1–6 respectively. Anti-E2$^c$ at 1 ug/ml (lane ( ) and VEE HMAF at 1:1000 (lane 10) are positive controls, while irrelevant isotype-matched MAbs at 1 ug/ml (lanes 7 and 8) are negative controls. High and low molecular weight markers are labeled on the right.
Figure 3B:
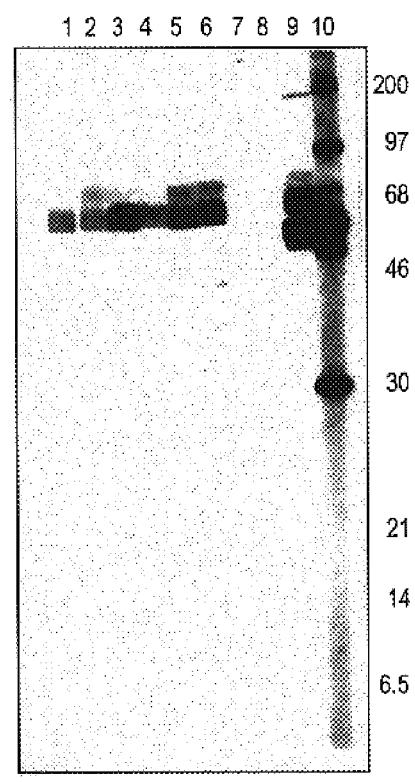

Biochemical characterization of the Mabs to V3526. Spleen cells from BALB/c mice vaccinated with V3526 were used to produce hybridomas. Supernatants from these hybridomas were tested for binding to V3526 and to V3000, the virulent infectious clone from which V3526 was derived. Six hybridomas were chosen for study on the basis of binding better to V3526 than to V3000 in ELISA (FIG. 1). These six Mabs immunoprecipitated PE2 and E1, but not E2, from TrD-infected cell lysates (FIG. 2B), and PE2 and E1 from V3526-infected cell lysates (FIG. 2A). A smaller protein (approximately 11 kDa) was also immunoprecipitated by four Mabs from TrD-infected cells (FIG. 2B). Western blot analysis indicated that these Mabs reacted with PE2 and not E1 (FIG. 3). Competitive binding studies performed using Mabs labelled with biotin indicated that all six Mabs were in one competition group, although Mabs 5E2 and 5E4 required higher concentrations to effectively compete for binding with the other four Mabs (data not shown).

Figure 4:
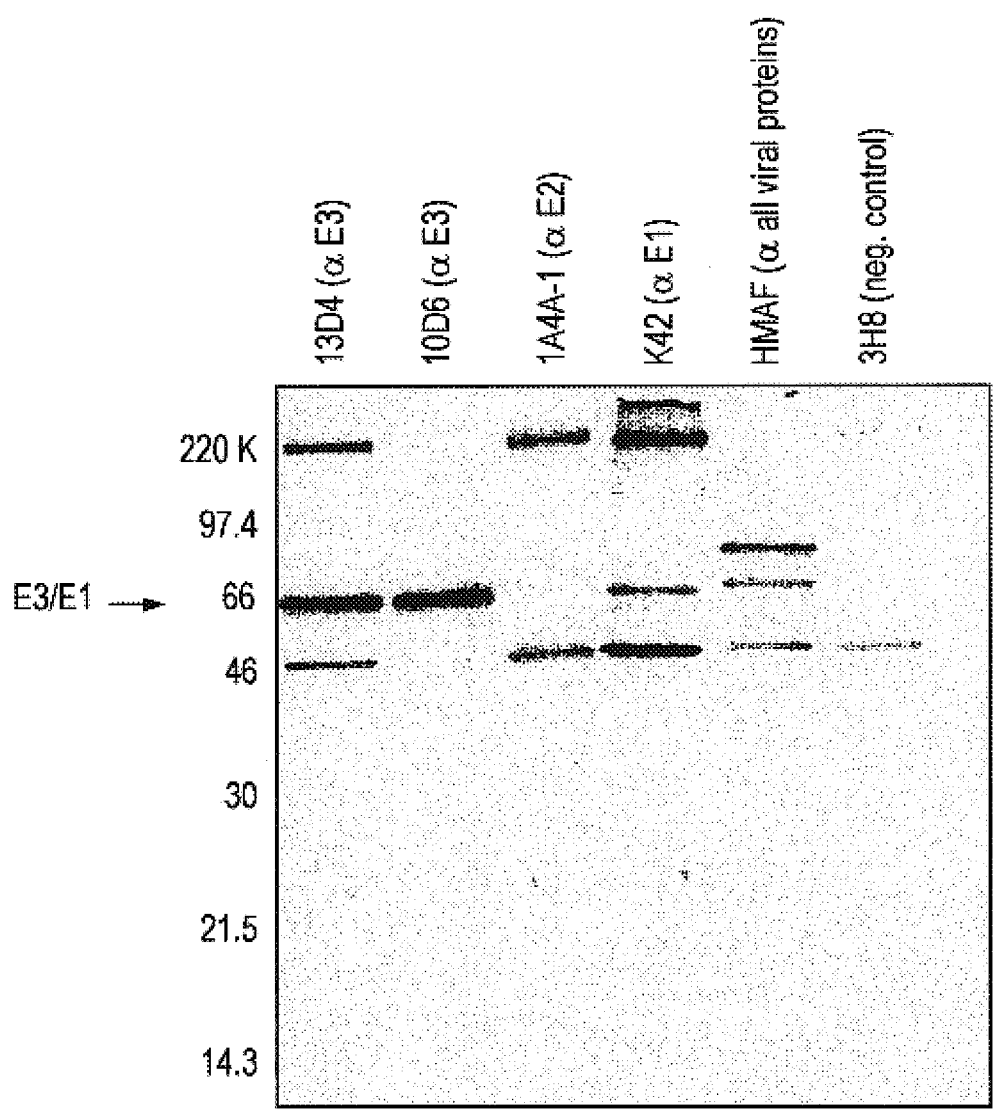
FIG. 4. Reactivity of MAbs with E3/E1 protein in western blot. A recombinant VEE virus E3-E1 protein was electrophoresed on a 12% polyacrylamide gel and transferred to nitrocellulose. Reactivity of E3-specific Mabs 13D4 (lane 1), 10D6 (lane 2), E2-specific MAbs 1A4A-1 (lane 3), E1-specific MAb K42 (lane 4), VEE-specific hyperimmune ascitic fluid (HMAF, lane 5) and a VEE-nonreactive control MAb 3H8 (lane 6) are shown. The E3-E1 recombinant protein has an apparent molecular weight (shown on left) of 66 kDa and is bound by MAbs to E3 and E1, but not E2, and is bound by polyvalent HMAF.

The reactivity of the Mabs with PE2, but not E2, suggested that these Mabs were specific for the E3 protein. A VEE virus replicon was constructed to express an E3:E1 construct in which the E3 glycoprotein, without the cleavage sequence, was translated with the VEE E1 glycoprotein instead of the E2 glycoprotein. Two Mabs, 13D4 and 10D6, were tested and observed to react with this protein in western blot (FIG. 4).

Synthetic peptides spanning the entire E3 sequence were synthesized either as free peptides or bound to nitrocellulose membranes. No reactivity with the Mabs was observed using peptides as the antigen or as a binding competitor in ELISA or by incubating the Mabs with the spots membranes (data not shown). Truncated E3 proteins that deleted the cysteine at position 49 or the cysteines at positions 16 and 22 were not bound by the MAb. Studies to look at individual cysteines are in progress, but the results suggest the cysteines and glycosylation are important and the epitope is probably conformational but can reform on nitrocellulose.

The MAb binds and inhibits plaque formation by VEE-IE 1150 k, but not WEE cBA and testing is in progress on E3-retaining EEE and VEE IIIA viruses (not shown).

EXAMPLE 2

Functional characterization of the Mabs. The Mabs were tested for the ability to neutralize virus in a plaque reduction test. All six Mabs neutralized V3526, with Mab 13D4 being the most effective, requiring at least 5-fold less protein than the other MAbs (Table 1). Only Mab 13D4 neutralized virulent V3000 or TrD viruses, but required 300-fold more Ab to neutralize the virulent virus compared to V3526. The addition of complement to the neutralization assay did not change the endpoint neutralization titers of the E3-specific Mabs (Table 1). Mab 1A4A-1, anti E2$^c$ used as a positive control, neutralized all three viruses (Table 1).

TABLE 1

Neutralization of VEE virus by anti-V3526 MAbs with or without guinea pig complement

| | Virus | | | |
|---|---|---|---|---|
| | V3526 | | TrD | |
| | Endpoint Neutralization Concentration (ug/ml) | | | |
| MAb | C'$^a$ | no C' | C' | no C' |
| 3F2 | 0.2 | 0.2 | >10 | >10 |
| 5E2 | 0.3 | 0.6 | >10 | >10 |
| 10D6 | 0.2 | 0.3 | >10 | >10 |
| 10D7 | 0.2 | 0.3 | >10 | >10 |
| 13D4 | 0.2 | 0.3 | >10 | >10 |
| 5E4 | 0.04 | 1 | >10 | >10 |
| E2$^c$ | 0.00001 | 0.001 | 0.003 | 0.002 |
| IgG$_{2a-2b}$$^b$ | >10 | >10 | >10 | >10 |

PRNT were performed against uncloned TrD virus and vaccine strain V3526.
$^a$C1 guinea pig complement at a final concentration of 5% was added.
$^b$Isotype controls were tested individually and had the same results.
Anti-E2$^c$ was used as a positive control.

The protective efficacy of these Mabs was evaluated by administration of purified Mab one day before subcutaneous challenge with 1×10$^4$ PFU of virulent TrD virus. Passive transfer of at least 20 ug of Mab 13D4 into naive BALB/c mice protected the mice from death after challenge (Table 2). The other five Mabs generally protected fewer than half of the recipient mice, even when 50 ug MAb was administered, although the mean time to death was extended significantly (p<0.001) in these mice relative to control mice.

TABLE 2

Survival after TrD$^a$ challenge by BALB/c mice passively inoculated with MAbs

| | Amount of MAb given (ug/mouse)$^b$ #Survived/#tested (GMT in ELISA)$^c$ | | | |
|---|---|---|---|---|
| Transferred MAb | 50 | 20 | | 2 |
| 13D4 | 5/5 (8778) | 9/9 (5432) | 7/7 (2400) | 1/9 (ND) |
| 5E2 | 0/5 (1949) | 1/9 (2208) | | |
| 5E4 | 6/6 (19858) | 1/5 (2208) | 2/9 (2697) | |
| 10D6 | 1/5 (5653) | 1/9 (1808) | | |
| 10D7 | 2/5 (6400) | 2/9 (1998) | | |
| 3F2 | 1/5 (1600) | 8/9 (9897) | 0/8 (1258) | 0/5 (1596) | 0/9 (ND) |
| E2c$^d$ | 5/5 (2441) | 8/8 (1339) | 5/5 (800) | |
| IgG2a–2b$^e$ | 0/5 (<100) | 0/9 (<100) | 0/9 (<100) | |

$^a$10$^4$ PFU of TrD were given ip per mouse in 0.2 ml of PBS at 25 hours post-transfer of MAb.
$^b$MAb was given ip in 0.2 ml of PBS
$^c$Sera were obtained 20 house post-transfer of MAb and tested in ELISA on V3526. All mice given 20 and 50 ug/mouse of MAb were positive for VEE Ab.
$^d$MAb anti-E2$^c$ was used as a positive control.
$^e$Irrelevant isotype-matched MAbs were used as negative controls.

This is the first demonstration of protection afforded by an Mab specific for an epitope on the VEE virus E3 protein. Protection by this MAb is surprising, given that the E3 glycoprotein has been suggested to be cleaved intracellularly by a furin-like enzyme in a post-golgi compartment. The fate of the E3 protein after cleavage is not known, but it has not been found to remain associated with the glycoprotein spikes on mature VEE virions as it does on the Semliki Forest alphavirus. The limited ability of these E3-specific Mabs to bind and neutralize virulent VEE virus in vitro might have suggested that they would not be efficacious against virulent virus challenge in vivo. However, the binding in ELISA was tested against purified mature virions that are expected to be free of E3, and it has previously been demonstrated that Mabs to E1 glycoprotein that do not neutralize in plaque reduction assays can protect against alphavirus challenge (Schmaljohn et al., 1982, Nature 297, 70–72).

The protection afforded by the E3-specific Mabs was not sterile, as new virus-specific antibody responses were detected in the sera of mice after challenge. Interestingly, the E2c-specific Mab used as a control in these studies did mediate nearly sterile immunity in recipient mice, as the challenged mice had no or very low titers (1:300) of VEE-specific antibodies of other isotypes.

The generation of murine Mabs to a previously unknown protective epitope after vaccination with the new V3526 vaccine candidate suggests that this may represent an improvement in VEE vaccine development. As this vaccine candidate continuously presents E3 to the immune system, it is likely that this vaccine strain would be more effective than PE2-cleaving vaccine strains at eliciting such protective Abs.

What is claimed is:

1. An isolated antibody which recognizes Venezuelan equine encephalitis alphavirus E3 glycoprotein.

2. A monoclonal antibody which recognizes an alphavirus E3 glycoprotein.

3. The antibody according to claim 2, wherein the antibody inhibits alphavirus infection in a subject in vivo.

4. The antibody according to claim 2, wherein the antibody ameliorates symptoms of alphavirus infection when said antibody is administered to a subject after infection with the alphavirus.

5. The antibody according to claim 2, wherein the antibody prevents disease from infection with an alphavirus when administered prior to infection with said alphavirus.

6. The antibody according to claim 2, wherein the antibody binds alphavirus in vitro.

7. The antibody according to claim 2, wherein the antibody immunoprecipitates PE2 from supernatants or cell lysates of cell cultures infected with alphavirus virus.

8. An isolated antibody which competes with the antibody of claim 7 for binding to E3.

9. The antibody according to claim 2, wherein said antibody is chosen from the group consisting of: monoclonal antibody 13D4 produced from hybridoma VE-V 13D4-1-1 having ATCC accession no; PTA-4248, monoclonal antibody 5E2 produced from hybridoma VE-V 5E2-1-1 having ATCC accession no. PTA-5813 and monoclonal antibody 10D6 produced from hybridoma VE-V 10D6-1-1 having accession no. PTA-5814.

10. An isolated antibody which competes with the antibody of claim 9 for binding to E3.

11. A mixture comprising one or more antibodies selected from the group consisting of:

5E2,

10D6,

; and

13D4.

12. A mixture according to claim 11 wherein said mixture prevents alphavirus infection in a subject upon administration to said subject.

13. A therapeutic composition for ameliorating symptoms of alphavirus infection comprising any of MAb 13D4, 5E2, and 10D6, and a pharmaceutically acceptable excipient.

14. A passive vaccine against alphavirus infection comprising any of MAb 13D4, 5E2, and 10D6.

15. An anti-VEE composition, comprising any of 13D4, 5E2, and 10D6 monoclonal antibody in an amount effective for inhibiting VEE infection, and a pharmaceutically acceptable carrier.

16. A monoclonal antibody producing cell line that produces a monoclonal antibody according to claim 2.

17. The cell line according to claim 16, producing a monoclonal antibody selected from the group consisting of 13D4, 5E2, and 10D6.

18. A method of treating VEE virus infection comprising administering to a patient in need of said treatment an effective amount of a composition comprising any of 13D4, 5E2, and 10D6 monoclonal antibody.

19. A method for detecting, in a sample, VEE virus which does not cleave E3, said method comprising:

(i) incubating the sample with an effective amount of at least one monoclonal antibody according to claim 2, under conditions which allow the formation of an antibody-VEE virus complex; and (ii) detecting the antibody-E3 virus complex wherein the presence or absence of the complex indicates the presence or absence of said VEE virus in the sample.

20. A method for detecting VEE virus according to claim 19 wherein, said monoclonal antibody is chosen from the group consisting of MAb 13D4, MAb 5E2, and MAb 10D6.

21. The method according to claim 19, wherein said monoclonal antibodies compete for binding to E3 with an antibody chosen from the group consisting of MAb 13D4, MAb 5E2, and MAb 10D6.

22. A method for detecting VEE virus according to claim 19, wherein said sample is a biological sample.

* * * * *